US006869453B1

(12) United States Patent
Lewis et al.

(10) Patent No.: US 6,869,453 B1
(45) Date of Patent: Mar. 22, 2005

(54) REACTIVE DYE COMPOUNDS

(75) Inventors: David Malcolm Lewis, Otley (GB); Dong Wei He, Leeds (GB); Taher Iqbal Yousaf, Egham (GB); Gilles Yves Marie Fernand Genain, London (GB)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/089,339

(22) PCT Filed: Sep. 29, 2000

(86) PCT No.: PCT/US00/26974

§ 371 (c)(1),
(2), (4) Date: Mar. 27, 2002

(87) PCT Pub. No.: WO01/25337

PCT Pub. Date: Apr. 12, 2001

(30) Foreign Application Priority Data

Oct. 1, 1999 (GB) ............................................. 9923329

(51) Int. Cl.[7] .............................................. D06P 1/382
(52) U.S. Cl. ....................... 8/404; 8/405; 8/436; 8/543; 8/917; 8/918; 8/924
(58) Field of Search ........................... 8/404, 405, 436, 8/543, 917, 918–925, 549

(56) References Cited

U.S. PATENT DOCUMENTS

| | | |
|---|---|---|
| 3,116,275 A | 12/1963 | Gamlen et al. |
| 3,377,336 A | 4/1968 | Siegel et al. |
| 3,433,781 A | 3/1969 | Ackerman et al. |
| 3,522,246 A | 7/1970 | Siegel et al. |
| 3,527,760 A | 9/1970 | Siegel et al. |
| 3,873,513 A | 3/1975 | Kullman et al. |
| 4,092,478 A * | 5/1978 | Plant et al. |
| 4,098,784 A | 7/1978 | Swidler et al. |
| 4,139,345 A * | 2/1979 | Crabtree et al. |
| 4,150,021 A | 4/1979 | Swidler et al. |
| 4,832,698 A | 5/1989 | Ikeou et al. |
| 4,855,411 A | 8/1989 | Thompson et al. |
| 4,898,933 A | 2/1990 | Schläfer et al. |
| 5,037,449 A | 8/1991 | Hoegerle et al. |
| 5,175,263 A | 12/1992 | Schläfer et al. |
| 5,548,071 A | 8/1996 | Deitz et al. |
| 5,766,267 A | 6/1998 | Schumacher et al. |
| 5,877,310 A | 3/1999 | Reddington et al. |
| 6,350,862 B1 | 2/2002 | Brock et al. |
| 6,398,822 B1 | 6/2002 | Brock et al. |

FOREIGN PATENT DOCUMENTS

| | | |
|---|---|---|
| CA | 771632 | 11/1967 |
| DE | 33 35 956 A1 | 4/1985 |
| DE | 196 45 601 A | 5/1998 |
| EP | 0 260 806 A2 | 3/1988 |
| EP | 0 735 107 A2 | 9/1990 |
| EP | 0 418 623 A1 | 3/1991 |
| FR | 1 274 732 A | 2/1962 |
| GB | 949 316 A | 2/1964 |
| GB | 1 020 304 | 2/1966 |
| GB | 1 060 734 | 3/1967 |
| GB | 1 275 944 | 6/1972 |
| GB | 1 414 420 A | 11/1975 |
| JP | 60 208 367 | 10/1985 |
| JP | 63 006 181 | 1/1988 |
| WO | WO-96/02593 | 2/1996 |
| WO | WO 97 19188 A | 5/1997 |
| WO | WO 99/51685 | 10/1999 |
| WO | WO 99/51686 | 10/1999 |
| WO | WO 99/51689 | 10/1999 |
| WO | WO 00/69973 | 11/2000 |
| WO | WO 00/69974 | 11/2000 |
| WO | WO 01/25336 | 4/2001 |
| WO | WO 01/25338 | 4/2001 |
| WO | WO 01/25339 | 4/2001 |

OTHER PUBLICATIONS

I. Grabtchev, "The Synthesis and Properties of some Triazine–stilbene Fluorescent Brighteners", Dyes Pigm., 1994, pp. 249–254, 25.

The Journal of Macromelecular Chemistry, 1976, 50, pp. 1–8, 728.

The Journal of Macromolecular Chemistry, 1977, 64, pp. 205–210, 951.

S. Horrobin, "The Hydrolysis of Some Chloro–1,3,5–Triazines", The Journal of the Chemical Society, 1963, pp. 4130–4144.

F. Lehr, "Synthesis and Application of Reactive Dyes with Heterocyclic Reactive Systems," Jan. 19, 1990, pp. 239–263.

* cited by examiner

Primary Examiner—Margaret Einsmann
(74) Attorney, Agent, or Firm—Jenkins, Wilson & Taylor, P.A.

(57) ABSTRACT

A reactive dye compound comprising: (a) at least one chromophore moiety; (b) at least one nitrogen-containing heterocycle; (c) a linking group to link each chromophore moiety to each nitrogen-containing heterocycle; characterised in that at least one nitrogen-containing heterocycle is substituted with at least one Y group wherein Y is a phosphonate or a borate derivative. The compounds herein have high Exhaustion Values (E), high Fixation Values (F) and high Efficiency Values (T) and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require less levels of salt for dyeing cotton substrates.

25 Claims, No Drawings

REACTIVE DYE COMPOUNDS

TECHNICAL FIELD

The present invention relates to reactive dye compounds. In particular the present invention relates to reactive dye compounds having improved dye-bath Exhaustion (E) and improved dye-fibre covalent Fixation (F).

BACKGROUND OF THE INVENTION

Reactive dye compounds are known in the art for dyeing various substrates. Such substrates include for example proteinaceous materials such as keratin, e.g. found in hair, skin and nails and various animal body parts such as horns, hooves and feathers, and other naturally occurring protein containing materials, e.g. silk and saccharide-derived materials such as those derived from cellulose or cellulose derivatives, e.g. natural products such as cotton, and synthetic fibres such as polyamides.

Examples of classes of such reactive dyes which are well known in the art include dyes containing a mono- or dichloro- or fluoro-1,3,5-triazinyl group, trichloro or mono- or di-fluoro-pyrimidyl group, beta-halogen-propionyl group, beta-halogenoethyl-sulphonyl group, beta-halogenoethylsulphamyl group, chloroacetyl amino, beta-(chloro-methyl)-beta-sulphatoethylsulphamyl group, or a vinyl sulphonyl group.

In the case of the dyes containing a triazinyl group or a pyrimidyl group, in place of the reactive halogen atoms one can use other groups which dissociate in the presence of alkali. Canadian Patent 771632, for example, discloses examples of such other groups including sulphonic acid, thiocyanate, sulphophenoxy, sulphophenyl thio, nitrosulphophenoxy groups, and quaternary ammonium groups.

"The Synthesis and Properties of some Triazine-Stilbene Fluorescent Brighteners", I.Grabtchev, discloses the synthesis of certain triazine stilbene fluorescent brighteners containing methacrylic groups.

The Journal of Macromoleular Chemistry 64 (1977), 205–210 (Nr. 951) discloses the polymerisation of acrylonitrile in dimethylformamide in the presence of some unsaturated triazine derivatives. The Journal of Macromolecular Chemistry 50 (1976) 1–8 (Nr.728) discloses the polymerization of styrene in the presence of some coloured anthraquinone and azoderivatives of 1,3,5-triazine, containing a group able to copolymerize.

The Journal of the Chemical Society, 1963, pages 4130–4144, "The Hydrolysis of Some Chloro-1,3,5-Triazines" by S. Horrobin, discloses that dichloro-m-sulphoanilinotriazine is rapidly hydrolysed in acetate (pH 4.7) or phthalate (pH 4.0) buffers.

There are many different types of commercially-available reactive dyes for dyeing cellulosic and polyamide-type substrates. However, a critical problem still facing the textile dye industry today is the significant level of dyestuff material which remains in the effluent waste water after the dyeing process is finished. The industry measure for this problem is known as dye-bath Exhaustion (E). A high Exhaustion value for a particular dye compound means that a low level of spent dye remains in the effluent after the dyeing process is complete, while a low Exhaustion value means that a high level of spent dye remains in the effluent. There is clearly a need therefore for new dye compounds which have higher Exhaustion Values compared with commercially available dye compounds, and which provide benefits in terms of reducing levels of spent dyestuff in effluent water.

As well as having a high Exhaustion Value, it is also important for a dye compound to have a high dye-fibre covalent Fixation Value (F). The Fixation Value (P) of a reactive dye compound is a measure of the extent of covalent bonding with the substrate based on the dye originally absorbed during the dyeing process. Thus 100% Fixation means that 100% of the absorbed dye covalently bonds to the substrate. Thus, there is clearly a need to provide dye compounds having increased Fixation Values. A high Fixation Value can result in a simplification of the post dyeing "soaping off process" traditionally associated with fibre reactive dye compounds. In particular, a high Fixation Value can result in a reduced time spent on the "soaping off process" together with a reduced cost.

It has now been surprisingly found that a new class of fibre reactive dye compounds comprising a nitrogen-containing heterocycle substituted with at least one phosphonate derivative, exhibit significantly increased values of Exhaustion (E) and Fixation (F). These dyes can be used on a wide variety of substrates. They are particularly useful for cellulosic substrates, such as cotton, and materials such as keratin, hair, wool and silk, and show significant improvements in terms of reducing spent dyestuff in effluent, increasing dye affinity to the substrate, increasing the efficiency of the dye-substrate covalent reaction, and simplifying the post dyeing "soaping off process" traditionally associated with reactive dyes. In addition, the compounds of the present invention provide significantly more intense dyeings, and can be used for both high and low temperature dyeing, hence reducing the cost of the dyeing process. Furthermore, the compounds of the present invention can be used together with specific chromophores for cellulose substrate dyeing leading to significantly reduced levels of salt needed for dyeing.

SUMMARY OF THE INVENTION

According to the present invention there is provided a reactive dye compound comprising:
  (a) at least one chromophore moiety;
  (b) at least one nitrogen-containing heterocycle
  (c) a linking group to link each chromophore moiety to each nitrogen-containing heterocycle;
characterised in that at least one nitrogen-containing heterocycle is substituted with at least one Y group wherein Y is a phosphonate derivative or borate derivative, preferably wherein the phosphonate derivative is selected from polyphosphonate groups preferably having a formula —O—(P=O)(OH)R' wherein R' is any suitable nucleophile but is not OH.

The compounds of the present invention exhibit increased Exhaustion (E) and Fixation (F) values and provide improvements in terms of reducing spent dyestuff in effluent, increasing dye affinity to the substrate, increasing the efficiency of the dye-substrate covalent reaction, ability to carry out the long-liquor dyeing process at room temperature as well as at elevated temperatures, and simplifying the post dyeing "soaping off process" traditionally associated with fibre reactive dyes. In addition, the compounds of the present invention provide significantly more intense dyeings, i.e. greater colour intensity in the dyed substrate, without compromising levelness. Typical Exhaustion Values for the compounds and products herein are greater than 95%. Typical Fixation Values for the compounds and products herein are greater than 95%.

DETAILED DESCRIPTION OF THE INVENTION

As used herein the term "reactive dye" means a dye containing one or more reactive groups, capable of forming covalent bonds with the substrate to be dyed, or a dye which forms such a reactive group in situ.

As used herein the term "Exhaustion" in relation to reactive dyes means the percentage of dye which is transferred from a solution of the dye to the substrate to be treated at the end of the dyeing process, before rinsing and soaping. Thus 100% Exhaustion means that 100% of the dye is transferred from the dye solution to the substrate. Typical Exhaustion Values for the dye compounds herein are >95%.

As used herein the term "Fixation" in relation to reactive dyes means the percentage of dye which covalently bonds with the substrate, based on the dye originally absorbed during the dyeing process. Thus 100% Fixation means that 100% of the dye absorbed is covalently bonded with the substrate. Typical Fixation Values for the dye compounds herein are 95%.

The total efficiency of reactive dyes can be measured by their Efficiency Value (T) which can be calculated from the Exhaustion Value (E) and Fixation Value (F) using the following equation:

% $T=(F \times E)/100$

The compounds of the present invention comprise a chromophoric moiety and a nitrogen-containing heterocycle linked via a linking group. The nitrogen-containing heterocycle is substituted by at least one Y group wherein Y is a phosphonate or borate derivative.

Chromophoric Moiety

The reactive dye compounds herein can comprise one or more chromophoric moieties (D or D'). In reactive dye compounds comprising two or more chromophoric moieties these can be the same or different. Preferably the reactive dye compounds herein comprise from one to three chromophoric moieties.

Any chromophoric moieties suitable for use for dyeing substrates can be used in the present invention. The term chromophore as used herein means any photoactive compound and includes any coloured or non-coloured light absorbing species, eg. fluorescent brighteners, UV absorbers, IR absorbing dyes.

Suitable chromophoric moieties for use in the dye compounds herein include the radicals of monoazo, disazo or polyazo dyes or of heavy metal complex azo dye derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye.

Suitable chromophoric moieties for use in the dye compounds herein include those disclosed in EP-A-0,735,107 (Ciba-Geigy), incorporated herein by reference, including the radicals described therein which contain substituents customary for organic dyes, such as sulphonate substituents which enhance the water-soluble properties of the dye compound.

Most preferred chromophoric D or D' groups for use herein are polysulphonated azo chromophores such as those present in Procion (RTM) dyes commercially available from BASF, Drimalan (RTM) dyes commercially available from Clariant, Drimarene (RTM) dyes commercially available from Clariant and Levafix (RTM) dyes commercially available from Dystar.

Nitrozen-containing Heterocycle

The reactive dyes of the present invention comprise at least one nitrogen-containing heterocyclic moiety. In reactive dye compounds containing two or more nitrogen-containing heterocycles these can be the same or different. Preferably the reactive dye compounds herein comprise from one to three nitrogen-containing heterocycles. At least one of the nitrogen-containing heterocycle moieties herein is substituted with at least one Y group defined below.

Suitable nitrogen-containing heterocycles for use herein include monocyclic, bicyclic or polycyclic, unsaturated heterocycles containing at least one nitrogen heteroatom. When monocyclic rings are used, they are preferably selected from unsaturated rings having from about 3 to about 7 ring atoms, especially 5 or 6 ring atoms, comprising from about 1 to about 3 nitrogen heteroatoms, preferably 2 or 3 nitrogen heteroatoms. When bicyclic heterocycles are used, they preferably comprise an unsaturated nitrogen containing heterocycle having 3 to 7 ring atoms, preferably an unsaturated nitrogen containing heterocycle having 5 or 6 ring atoms comprising 1 or 2 nitrogen atoms, fused to a 5 to 7 membered carbocycle preferably a 6-membered unsaturated carbocycle. When bicyclic heterocycles are used, the oxy- or thio- carbonyl substituents are preferably attached to the nitrogen-containing heterocyclic ring.

Preferred for use herein are 5 or 6 membered unsaturated nitrogen-containing monocyclic heterocyclic rings comprising 2 or 3 nitrogen heteroatoms or bicyclic rings containing a 5 or 6 membered unsaturated heterocyclic ring containing 2 nitrogen heteroatom fused to a 6 membered unsaturated carbocycle.

Examples of suitable heterocycles for use herein include, but are not necessarily limited to triazine, pyrimidine, quinoxaline, pyrimidinone, phthalazine, pyridazone and pyrazine.

Preferred for use in the compounds herein are triazine, pyrimidine and quinoxaline.

Linking Moiety

The compounds herein further comprise a linking moiety to link each nitrogen-containing heterocycle to each chromophoric moiety. Any linking moieties suitable for use in dyeing substrates can be used in the present invention. Preferably the linking moiety is selected from NR, NRC=O, C(O)NR, NRSO$_2$ and —SO$_2$NR wherein R is H or C$_1$–C$_4$ alkyl which can be substituted by halogen, preferably fluorine or chlorine, hydroxyl, cyano, C$_1$–C$_4$ alkoxy, C$_2$–C$_5$ alkoxycarbonyl, carboxyl, sulfamoyl, sulfo or sulfato. When the heterocycle is a triazine or pyrimidine a preferred linking moiety is NR, preferably where R is H or C$_1$–C$_4$ alkyl, more preferably where R is H or CH$_3$, especially H. When the heterocycle is quinoxaline or phthalazine, a preferred linking moiety is NRC=O, where R is H or C$_1$–C$_4$ alkyl, more preferably where R is H or CH$_3$, especially H.

Substituent Y

The nitrogen-containing heterocycle is substituted with at least one Y group wherein Y is a phosphonate or borate derivative. Preferred phosphonate derivative are polyphosphonate derivatives having the formula —O—(P=O)(OH) R' wherein R' is any suitable nucleophile group which is not OH.

As used herein the term "nucleophilic group" means a negative ion or any neutral molecule that has an unshared electron pair. Preferred nucleophilic groups herein can be selected from NH$_2$, SH, COOH, —N=, NHR$^1$ and NR$^1$R$^2$ wherein R$^1$ and R$^2$ may be the same or different and may be selected from C$_1$–C$_4$ alkyl.

Suitable R' groups for use herein are alkyl or aryl residues which contain at least one nucleophilic group. Preferably the R' groups herein are selected from the following groups each substituted with or containing at least one nucleophilic group: substituted or unsubstituted, straight chain or branched chain $C_1$–$C_8$ alkyl, substituted or unsubstituted straight chain or branched chain $C_2$–$C_8$ alkenyl having at least one olefinic group, substituted or unsubstituted, saturated or unsaturated or aromatic 3–9 atom monocyclic carbocycle or substituted or unsubstituted, saturated or unsaturated or aromatic 7–17 polycyclic carbocycle, substituted or unsubstituted, saturated or unsaturated or aromatic 3–9 atom monocyclic heterocycle or substituted or unsubstituted, saturated or unsaturated or aromatic 7–17 atom polycyclic heterocycle, wherein said heterocycles each have one or more heteroatoms selected from O, N or S.

In the definition of R' above, where the term "substituted" is used such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, aryl, cycloalkyl, heteroaryl, heterocycloalkyl, (e.g. piperidinyl, morpholinyl, piperazinyl, pyrrolidinyl, etc.), imino, thioxo, hydroxyalkyl, aryloxy, arylalkyl, and combinations thereof.

Preferred R' groups for use herein include, but are not limited to, $CF_3$, $(CH_2)_nSH$, $(CH_2)_nNH_2$, $CH(CH_3)OH$, $C(OH)(CH_2COOH)_2$, $CH_2C(OH)(CO_2H)CH_2$ $COOH$, $(CH_2)_nNHR1$, $CH_2NR_1R_2$, $CH_2NHNH_2$, $CH_2NHOH$, $CH_2SMe$, $CH(NH_2)(CH_2)_n(COOH)$, $CH(NH_2)CH_2SMe$, $CH(NH_2)CH_2SSCH_2CH(NH_2)COOH$, 2-aminophenyl, 2-hydroxynaphthyl, 2-pyrrolidyl, $CH_2SSCH_2CO_3^-$, $(CH_2)_n$ $—SO_3^-$, $CH(NH_2)CH_2SO_3H$, $C_6H_4OR$, $C_6H_4COOH$, $C_6H_4NH_2$, $C_5H_4N$, $(CH_2)_nC_5H_4N$, $CH(R\#)NH_2$, $(CH_2)_n—$ $SSO_3^-$ $(CH_2)_n—S—S—(CH_2)_n$ $—C(OH)(H)C(OH)(H)$ $COOH$, $—C(OH)(H)CH_2COOH$, $C(OH)(COOH)$ $CH_2COOH$, $CH_2(H)(OH)COOH$, derivatives of hydroxy carboxylic acid polymerisation, eg. in the case of lactic acid dimerisation R' is $CH(CH_3)O(CO)CH(CH_3)OH$, R' groups derived from peptide or polypeptide and attached to the heterocyclic group via their terminal carboxylic group, wherein $R_1$ and $R_2$ is independently selected from $C_1$–$C_4$ alkyl, wherein n is an integer in the range of 1 to 4 wherein within the same molecule n is not necessarily the same integer and where R# corresponds to an amino acid sidechain. For examples of such amino acids, cf. "Organic Chemistry" by Graham Solomons, 5$^{th}$ Edition, Wiley, N.Y., 1992, p1094–1095.

Particularly preferred Y groups herein are groups derived from phosphonate compounds such as aceto phosphonic acid. A preferred Y group herein is a group derived from aceto phosphonic acid, namely $—O—PO(OH)C(CH_3)(OH)PO(OH)2$.

Preferred reactive dye compounds of the present invention may be represented by the following formula (I):

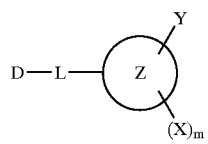

wherein:
D is a chromophoric group;
L is a linking moiety selected from NR, $N(C=O)R$, $N(SO_2)R$;

R is H or $C_1$–$C_4$ alkyl which can be substituted by halogen, hydroxyl, cyano, $C_1$–$C_4$ alkoxy, $C_2$–$C_5$ alkoxycarbonyl, carboxyl, sulfamoyl, sulfo, sulfato;
Z is a nitrogen-containing heterocycle;
Y is a phosphonate or borate derivative.
X is selected from Y (e.g. bis-phosphonate compounds), thio-derivatives, halogen (preferably fluorine and chlorine), amines, alkoxy groups, carboxylic acid groups, $CN$, $N_3$ and quaternized nitrogen derivatives, Q+;
m is 1 or 2 (depending on the Z group, for example m is 1 when Z is triazine and m is 2 when Z is pyrimidine).

Suitable thio-derivatives for use herein include, but are not necessarily limited to, groups having the formula SR' wherein R' is selected from H or alkyl or preferably short chain alkyl (preferably less than about 6 carbon atoms), alkanol, alkyl carboxylate, alkylamide, alkylsulphonate, alkyl phosphonate, alkyl thiosulphonate, alkylamine, alkyl thiosulphate, aryl sulphonate, aryl carboxylate, aryl phosphate, aryl amine, cyanates, sulphonates, branched alkyl thio carboxylates, branched alkanol thiols, guanides, alkyl-α-amino-α-carboxylate, (di) thio alkyl esters of glycerol, alkyl thiol alkyl esters of glycerol, alkyl esters, mono thio diesters, thiol alkyl esters of ethylene glycol, alkyl thiol alkyl ester of ethylene glycol and alkyl thiolipoates. Preferably R' is selected from alkyl carboxylates, alkanols and alkylamines.

Examples of suitable thio-derivatives include SR' groups where R' is selected from $C_1$–$C_4$ alkyl, $(CH_2)_nCOOH$, $(CH_2)_nCONH_2$, $(CH_2)_nSO_3H$, $(CH_2)_nCOOM$, $(CH_2)_nPO_3H$, $(CH_2)_nOH$, $(CH_2)_nSSO_3^-$, $(CH_2)_nNR''_2$, $(CH_2)_nN^+R''_3$, $PhSSO_3^-$, $PhSO_3H$, $PhPO_3H$, $PhNR''_2$, $PhN^+R''_3$, $—CN$, $SO_3^-$, $(CH_2)_2CH(SH)R''(CH_2)_3COOH$, $—CH_2CHOHCH_2SH$, and

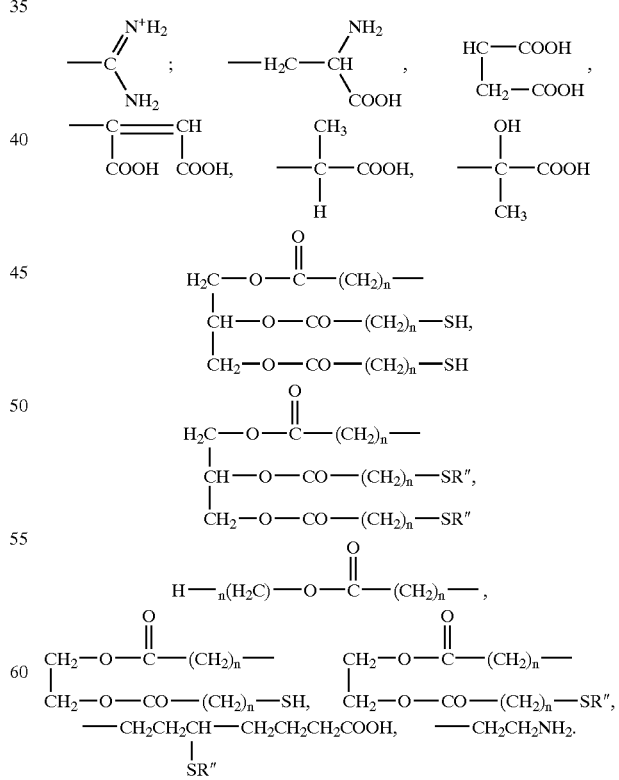

n is an integer in the range of 1 to 4 wherein within the same molecule n is not necessarily the same integer; and M is a cation of alkaline earth metal, alkali metal, $NH_4^+$ or $NR''_3^+$ and wherein R" is $C_1$–$C_4$ alkyl.

Preferred thio-derivatives for use herein have the formula SR' wherein R' is $(CH_2)_n COOH$, $(CH_2)_n OH$, and $(COOH)CH_2CH_2(COOH)$, wherein n is an integer from 1 to 4.

Especially preferred for use herein are thioglycolate ($R'=CH_2COOH$) thioethanol ($R'=(CH_2)_2OH$) and thiosuccinate ($R'=(COOH)CH_2CH_2(COOH)$), especially thioglycolate.

Suitable quaternized nitrogen derivatives for use herein can be represented by Q+ wherein Q is selected from amines, saturated or unsaturated, substituted or unsubstituted nitrogen containing heterocycles having from about 3 to about 8 ring members and comprising at least one nitrogen heteroatom. Preferred substituents are carboxylates, amides, $C_1$–$C_4$ and alkyl carboxylates.

Particularly preferred for use herein are Q groups selected from:

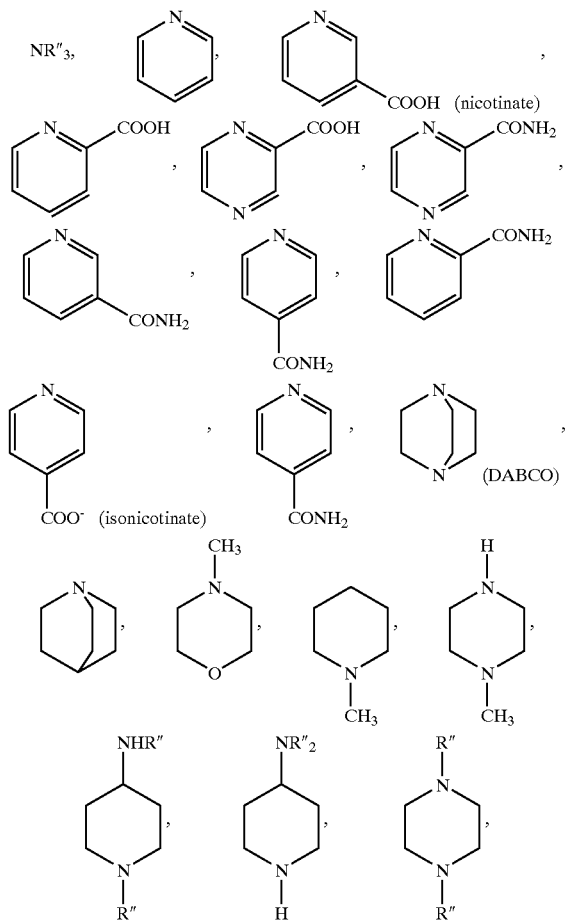

$(CH_3)_2N-NH_2$;
$N(CH_3)_2CH_2COOH$ (dimethylaminobetaine);
$N(CH_3)_2(CH_2)_nNH_2$
$N(CH_3)_2(CH_2)_nN^+R''_3$;
$N(CH_3)_2CH_2CONH_2$;

wherein R" is $C_1$–$C_4$ alkyl and n is an integer of from 1 to 4.

Particularly preferred quaternized nitrogen derivatives for use herein are nicotinate, diazabicyclooctane (DABCO), dimethylaminobetaine and isonicotinate, especially nicotinate.

The quatemized nitrogen derivative is attached to the nitrogen-containing heterocycle via its tertiary nitrogen atom.

Preferred X groups include Y, SR", halogen (preferably F or Cl), NR"H, NR"2, OR", COOH, SCN, SSO3, SO3, NR1R2, CN, N3 and quatemized nitrogen derivatives Q+, wherein R" is C1–C8 alkyl, or aryl and wherein Q, R1 and R2 are as defined above. Particularly preferred X groups for use herein are Y, halogen (fluorine and chlorine) and quaternized nitrogen derivatives.

A particularly preferred reactive dye compound of the present invention wherein the Y group in formula (I) above is derived from aceto phosphonic acid.

The present invention further relates to processes for the preparation of dyes herein. In general, dyes having the formula (I) can be prepared by reacting suitable precursors of the dye of formula (I) with one another, at least one of which contains a group D-L-Z, wherein D, L and Z are as defined above, and at least one of which contains a Y group (wherein Y is as defined above) and at least one of which contains an X group. It will be understood by those skilled in the art that in the case where X is halogen, then the halogen is part of the Z group in the starting materials e.g. dichlorotriazine.

For example, dye compounds of the invention having a formula (I) wherein Z is a triazine heterocycle can be prepared by reacting one mole of dichlorotriazine dye, such as those commercially available from BASF under the trade name Procion MX (RTM), with one mole of a suitable reactant containing a Y group and then reacting the intermediate dye compounds obtained with one mole of a suitable reactant containing an X group. It will be understood by those skilled in the art that when X is halogen, then the halogen is part of the starting material containing the Z group, e.g. dichlorotriazine, and no separate reaction with a reactant containing an X group needs to be carried out. It will also be understood by those skilled in the art that in the case where X is equal to Y (e.g. bis-phosphonate compounds) then one mole of dichlorotriazine dye can be reacted with two moles of a suitable reactant containing a Y group.

Dye compounds of the invention having a formula (I) wherein Z is a pyrimidine heterocycle can be prepared by reacting a difluoromonochloro pyrimidine dyes such as those commercially available from Clariant under the trade names Drimalan F (RTM) and Drimarene R or K (RTM), or a trichloropyrimidine dyes such as those commercially available from Clariant under the trade name Drimarene X, with a suitable reactant containing a Y group and then reacting the intermediate dye obtained with a suitable reactant containing an X group. As discussed above for triazines, it will be understood by those skilled in the art that when X is halogen, then the halogen is part of the starting material containing the Z group, e.g. difluoromonochloropyrimidine or trichloropyrimidine, and no separate reaction with a reactant containing an X group needs to be carried out. It will also be understood by those skilled in the art that in the case where X is equal to Y (e.g. bis-phosphonate compounds) then one mole of difluoromonochloro pyrimidine dye can be reacted with two moles of a suitable reactant containing a Y group.

Due to the assymetric nature of the pyrimidine heterocycle, dye compounds of the invention having a formula (I) wherein Z is a pyrimidine heterocycle can also be prepared by reacting a difluoromonochloropyrimidine dye such as those commercially available from Clariant under the tradenames Drimalan F (RTM) and Drimarene R or K (RTM), or a trichloropyrimidine dye such as those commercially available from Clariant under the trade name Drimarene X, with a suitable reactant containing a Y group and then reacting the intermediate dye obtained with a suitable reactant containing an X' group.

Dye compounds of the invention having a formula (I) wherein Z is a quinoxaline heterocycle can be prepared by reacting a dichloroquinoxaline dye such as those commercially available from Dystar under the tradename Levafix E (RTM), with a suitable reactant containing a Y group and then reacting the intermediate dye obtained with a suitable reactant containing an X group. It will be understood by those skilled in the art that when X is halogen, then the halogen is part of the starting material containing the Z group, e.g. dichloroquinoxaline, and no separate reaction with a reactant containing an X group needs to be carried out. It will also be understood by those skilled in the art that in the case where X is equal to Y (e.g. bis-phosphonate compounds) then one mole of dichloroquinoxaline dye can be reacted with two moles of a suitable reactant containing a Y group.

Preferred dye compositions herein comprise an acidic buffer material. Any acidic buffer suitable for use in reactive dye compositions can be used herein. An example of a suitable buffer is a mixed phosphate buffer.

When the dye composition herein is in the form of a paste a preferred ingredient is a thickening agent. Any suitable thickening agents suitable for use in reactive dye compositions can be used herein.

When the dye composition is in the form of an aqueous solution or aqueous gel/paste, the dye composition preferably has a pH of from about 2 to about 8.

The dyeing and printing processes which can be used with the dyes herein are conventional processes which are well known and which have been widely described in the technical and patent literature. The dye compounds herein are suitable for dyeing cotton both by the exhaust method (long liquor) and also by various pad-dyeing methods, whereby the goods are impregnated with aqueous, salt-containing or salt-free dye solutions and the dye is fixed after an alkali treatment or in the presence of alkali, if appropriate with the application of heat. The dye compounds herein are also suitable for the cold pad-batch method, in which the dye together with the alkali is applied at the pad-mangle melting point and then fixed by several hours of storage at room temperature. After fixing, the dyeings are thoroughly rinsed with cold and hot water, if appropriate with the addition of an agent acting as a dispersant and promoting the diffusion of the non-fixed portions. The dyes of the present invention are also suitable for use in a number of other processes such as pad-steam and pad-bake and the like.

Thus in accordance with another aspect of the present invention there is provided a use of the reactive dyes of the present invention for dyeing and printing substrates such as cotton, wool, nylon, silk, keratin, hair, leather, paper and the like. The compounds herein can be used in methods of dyeing all of the substrates listed above by applying an aqueous solution of one or more of the reactive dyes of the present invention to the substrate to be dyed under suitable conditions of pH and temperature.

The following examples serve to illustrate the compounds and compositions of the present invention.

The starting compounds and components given in the examples below can be used in the form of the free acid or in the form of their salts with alkali metal cations. It is to be understood that mixtures of compounds may be obtained in the final product. In the Examples below the starting materials are all commercially available. Procion (RTM) dyes are available from BASF UK, P.O. Box 4, Earl Road, Cheadle Hulme, Cheshire, SK8 6QG, UK, Drimarene (RTM) and Drimalan (RTM) dyes are available from Clariant (Switzerland) Ltd., R&D Dyestuffs, Post Box, Building 88/1007, CH-4002 Basel, Cibacron (RTM) dyes are available from Ciba Specialty Chemicals Inc., R&D, Textile Dyes Division, K-410.312, CH-4002 Basel, and Levafix (RTM) dyes are commercially available from Dystar Textilfarben, GmbH & Co. Deutschland KG, BU-R/F & E, Werk Hochst, Building G834, D-65926 Frankfurt am Main, Germany.

EXAMPLE 1

0.005 moles of Procion Yellow MX-3R dye is dissolved in 150 ml of distilled water in a 400 ml flask. The temperature of the reaction system is adjusted and maintained at 0–5° C. The pH of the starting dye solution is adjusted to 5–5.5 using solid sodium carbonate. 0.005 moles of aceto diphosphonic acid (Briquest ADPA 60A) is dissolved in 50 ml of distilled water. The pH of this aceto diphosphonic acid solution is adjusted to around 4.5. The aceto diphosphonic acid solution is slowly added into the solution of Procion Yellow MX-3R dye. The rate of addition is such that the addition takes around 2 hours to complete. During the process of addition the temperature of the reaction system is maintained at 0–5° C. After addition of the aceto diphosphonic acid solution is complete, the reaction is allowed to continue for 4–5 hours. The endpoint of the reaction is indicated by the pH of the reaction system remaining constant for more than 5 minutes. At this point the final dye is obtained. Using 6N HCl, the pH of the system is then reduced to below 2.5 to terminate the reaction. KSCN (about 25% of the total solution) is then added to the reaction mixture in order to precipitate the dye product. Filtration using Whatman filter paper is then carried out. The precipitate is then washed with acetone for 5–6 times (about 50 ml of acetone used each time) to obtain the final dye product in fine powder form of deep yellow colour.

A possible synthetic mechanism for the reaction of the Procion dyes with acetophosphonic acid is as follows:

EXAMPLE 2

4 g of Levafix Goldgelb EG dye is dissolved in 150 ml of distilled water in a 400 ml flask. The temperature of the reaction system is adjusted and maintained at 60–65° C. The pH of the starting dye solution is adjusted to 4.5–5 using solid sodium carbonate. 1 g of aceto diphosphonic acid (Briquest ADPA 60A) is dissolved in 50 ml of distilled water. The pH of this aceto diphosphonic acid solution is adjusted to around 3–3.5. The aceto diphosphonic acid solution is slowly added into the solution of Levafix Goldgelb EG dye. The rate of addition is such that the addition takes around 3–4 hours to complete. During the process of addition the temperature of the reaction system is maintained at 60–65° C. After addition of the aceto diphosphonic acid solution is complete, the reaction is allowed to continue for 1–2 hours. The endpoint of the reaction is indicated by the pH of the reaction system remaining constant for more than 5 minutes. At this point the final dye is obtained. Using 6N HCl, the pH of the system is then reduced to below 2.5 to terminate the reaction. KSCN (about 25% of the total solution) is then added to the reaction mixture in order to precipitate the dye product. Filtration using Whatman filter paper is then carried out. The precipitate is then washed with acetone for 5–6 times (about 50 ml of acetone used each time) to obtain the final dye product in fine powder form of orange-yellow colour.

A possible synthetic mechanism for the reaction of the Levafix dyes with acetophosphonic acid is as follows:

EXAMPLE 3

0.005 moles of Drimalan Yellow FR dye is dissolved in 150 ml of distilled water in a 400 ml flask. The temperature of the reaction system is adjusted and maintained at 35–40° C. The pH of the starting dye solution is adjusted to 4.5–5 using solid sodium carbonate. 0.005 moles of aceto diphosphonic acid (or 2-hydroxyethane, 1,1-diphosphonic acid, Briquest ADPA 60A) is dissolved in 50 ml of distilled water. The pH of this aceto diphosphonic acid solution is adjusted to around 4.5. The aceto diphosphonic acid solution is slowly added into the solution of Drimalan Yellow FR dye. The rate of addition is such that the addition takes around 2 hours to complete. During the process of addition the temperature of the reaction system is maintained at 35–40° C. After addition of the aceto diphosphonic acid solution is complete, the reaction is allowed to continue for 4–5 hours. The endpoint of the reaction is indicated by the pH of the reaction system remaining constant for more than 5 minutes. At this point the final dye is obtained. Using 6N HCl, the pH of the system is then reduced to below 2.5 to terminate the reaction. KSCN (about 25% of the total solution) is then added to the reaction mixture in order to precipitate the dye product. Filtration using Whatman filter paper is then carried out. The precipitate is then washed with acetone for 5–6 times (about 50 ml of acetone used each time) to obtain the final dye product in fine powder form of deep yellow colour.

The compounds prepared according to Examples 1 to 3 and at standard depths all have high Exhaustion Values, high Fixation Values, particularly on cellulosic substrates such as cotton, and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require less levels of salt for dyeing cotton substrates. These advantages can be demonstrated by the following Examples 4 and 5.

EXAMPLE 4

All dye compounds prepared according to Examples 1 to 3 can be used to dye cotton using the dyeing procedures detailed below. After the cotton dyeing procedure has been carried out a soaping-off process can also be carried out on the cotton fibre.

Cotton Dyeing Procedure

An aqueous dye solution is prepared containing a dye compound according to any of Examples 1 to 3. The dye solution contains 1% on mass of fibre of dye, 80 g/L $Na_2SO_4$ and 5% on mass of fibre of sodium acetate. The cotton fabrics are soaked in water and then the cotton fabrics are dyed in the above dye-bath at pH 7 at 25° C. for 45 minutes. The dyed cotton fabric is then fixed in the dye-bath at pH 11.5 with addition of 30 g/L of trisodium phosphate and dyeing continued at 50° C. (25° C. for the Drimalan dye) for 60 minutes. The dyed fabric is rinsed with water.

In the above dyeing procedure the dye bath for each dye compound is almost totally exhausted (i.e. only slight colour in the dye bath after dyeing), indicating that the compounds prepared according to Examples 1 to 3 each have a high Exhaustion Value (>95%). The Exhaustion Values for each product can be obtained by comparing the photo-absorption of the dyebath liquid before and after dyeing. The Exhaustion Values for Examples 1 to 3 are given in Table A below.

Soaping-off Process

A soaping off process can then be carried out by washing the dyed fabrics with an aqueous solution of Sandozine NIE (2 g/L) (available from Clariant (Switzerland) Ltd., R&D Dyestuffs, Post Box, Building 88/1007, CH-4002 Basel) at 100° C. for 30 minutes.

In the above soaping-off process hardly any colour was removed from the fabric, resulting in an almost colourless soaping liquid, indicating that the compounds prepared according to Examples 1 to 3 each have a high degree of dye-fibre covalent bonding and a high Fixation Value (>95%). The Fixation Values of the dye products prepared according to Examples 1 to 3 are shown in Table A below.

From the Exhaustion and Fixation Values, the Efficiency Values can be calculated.

TABLE A

Exhaustion, Fixation and Efficiency Values for Examples 1 to 3

| Eg. | Exhaustion Value (E %) | Fixation Value (F %) | Efficiency Value (T) |
|---|---|---|---|
| 1 | 96.23% | 96.61% | 92.97 |
| 2 | 98.08% | 92.65% | 90.87 |
| 3 | 98.78% | 98.60% | 97.40 |

The E, F and T values of the dyes according to the present invention are typically higher than many of the commercially available starting materials. In particular, the F and T values of the dyes according to the present invention are significantly higher than those of the commercially available starting materials.

Co3 (International Standards Organisation) Wash Fastness Test

The dyed fabrics are washed with an aqueous solution containing ECE Reference Detergent (5 g/ml) and sodium carbonate (2 g/ml) at 60° C. for 30 minutes.

In the above wash fastness test, no noticeable colour was removed from the cotton fibre and no staining of the white adjacent fibres occurred (using Multiple Fibre adjacent strip supplied by the Society of Dyes and Colourists, Bradford, UK).

EXAMPLE 5

All dye compounds prepared according to Examples 1 to 3 can be used to dye nylon or wool using the dyeing procedures detailed below. After the nylon/wool dyeing procedure has been carried out a wash-test procedure can be carried out on the dyed fabric to test the wash-fastness of the dye compounds.

Wool/Nylon Dyeing Procedure

The wool/nylon fabric is soaked in a 2% w/w Alcopol-O (40% w/w sodium-d-isooctylsulpho-succinate commercially available from Allied Colloids) solution. The fabric is then dyed for 1 hour at 100° C. and pH 3.5 in a dye-bath containing the following compositions: 1.2% on mass of fibre of dye prepared according to any of Examples 1 to 3, 5% on mass of fibre of sodium acetate, 1% Albegal B (commercially available from Ciba). The dyed wool/nylon fabric was then rinsed with water.

In the above procedure intense dyeings are provided for each of the compounds prepared according to Examples 1 to 3.

Co2 (ISO) Wash Fastness Test Procedure for Wool/Nylon Fabrics

The dyed wool/nylon fabric is washed in an aqueous solution containing 5 g/L of ECE Reference Detergent (commercially available from the Society of Dyers and Colourists, Bradford, UK) at 50° C. for 45 minutes.

In the above wash fastness test, no noticeable colour was removed from the wool fibre and no staining of the white adjacent fibres occurred ((using multiple fibre adjacent strip supplied by SDC Bradford).

What is claimed is:

1. A reactive dye compound comprising:
   (a) at least one chromophore moiety;
   (b) at least one nitrogen-containing heterocycle;
   (c) a linking group, L, to link each chromophore moiety to each nitrogen-containing heterocycle;
   characterised in that at least one nitrogen-containing hetercycle is substituted with at least one Y group wherein Y is a phosphonate or a borate derivative,
   wherein the phosphonate derivative is selected from one of: $-O-(PO)(OH)C(CH_3)(OH)(PO)(OH)_2$, and $-O-(P=O)(OH)R'$ wherein R' is any suitable nucleophilic moiety, under the proviso that R' is not OH;
   wherein L is selected from the group consisting of NR, N(C=O)R, and N(SO$_2$)R;
   wherein R is H or $C_1$-$C_4$ alkyl, which further can be substituted by halogen, hydroxyl, cyano, $C_1$-$C_4$ alkoxy, $C_2$-$C_5$ alkoxycarbonyl, carboxyl, sulfamoyl, sulfo, sulfato.

2. A reactive dye compound according to claim 1 wherein Y is a phosphonate derivative selected from one of: $-O-(PO)(OH)C(CH_3)(OH)(PO)(OH)_2$ and $-O-(P=O)(OH)R'$ wherein R' is any suitable nucleophilic moiety, under the proviso that R' is not OH.

3. A reactive dye compound according to claim 1 wherein Y is $-O-(PO)(OH)C(CH_3)(OH)(PO)(OH)_2$.

4. A reactive dye compound according to claim 1 wherein the nitrogen-containing heterocycle is selected from triazine, pyrimidine, quinoxaline, phthalazine, pyridazone and pyrazine.

5. A reactive dye compound according to claim 1 wherein the nitrogen-containing heterocycle is selected from triazine, pyrimidine or quinoxaline.

6. A reactive dye compound according to claim 1 wherein the nitrogen-containing heterocycle is selected from triazine and pyrimidine.

7. A reactive dye compound according to claim 1 wherein the linking group is NR.

8. A reactive dye compound according to claim 7 wherein R is H or $C_1$-$C_4$ alkyl preferably H.

9. A reactive dye compound according to claim 1 wherein the nitrogen-containing heterocycle is additionally substituted with one or more X substituents, wherein X is independently selected from Y and halogen.

10. A reactive dye having the formula (I):

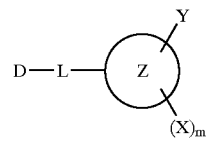

wherein D is a chromophore group;
L is a linking moiety selected from NR, N(C=O)R, N(SO$_2$)R;
wherein R is H or $C_1$-$C_4$ alkyl, wherein said alkyl can be further substituted by halogen, hydroxyl, cyano, $C_1$-$C_4$ alkoxy, $C_2$-$C_5$ alkoxycarbonyl, carboxyl, sulfamoyl, sulfo, and sulfato;
Z is a nitrogen-containing heterocycle;
Y is a phosphonate or borate derivative, wherein the phosphonate derivative is selected from one of: $-O-(PO)(OH)C(CH_3)(OH)(PO)(OH)_2$ and $-O-(P=O)(OH)R'$ wherein R' is any suitable nucleophilic moiety, under the proviso that R' is not OH;
X is selected from the group consisting of phosphonate derivatives, borate derivatives, thio-derivatives, halogen, amines, alkoxy groups, carboxylic acid groups, CN, $N_3$ and quaternized nitrogen derivatives, Q+;
m is 1 or 2;
and salts and esters thereof.

11. A method of dyeing a cellulosic substrate, comprising contacting the cellulosic substrate with a compound according to claim 1, wherein the cellulosic substrate is preferably cotton.

12. A method of dyeing wool, comprising contacting the wool with a compound according to claim 1.

13. A method of dyeing a polyamide substrates, comprising contacting the polyamide substrate with a compound according to claim 1, wherein the polyamide substrate is preferably nylon.

14. A method of dyeing silk, comprising contacting the silk with a compound according to claim 1.

15. A method of dyeing keratin, comprising contacting the keratin with a compound according to claim 1.

16. A method of dyeing leather, comprising contacting the leather with a compound according to claim 1.

17. Process for the preparation of a compound according to claim 1 comprising the steps of reacting a first starting material with a second starting material, the first starting material comprising at least one chromophore and at least one nitrogen-containing heterocycle which is attached to the chromophore group via a linking group L, the second starting material being a compound containing a Y group which is a phosphonate or borate group as defined hereinabove.

18. Process according to claim 17 wherein the second starting material is aceto phosphonic acid.

19. Process according to claim 17 wherein the process is carried out at a pH of from about 2 to about 8, preferably from about 3 to about 5.

20. Process according to claim 17 wherein the second starting material is added to the first starting material slowly, preferably dropwise, preferably over several hours, preferably 1 to 5 hours, more preferably 1 to 3 hours.

21. A dye composition comprising the compound of claim 1.

22. A dye composition according to claim 21 wherein the composition is in the form of a solid mixture and further comprises an acid buffer.

23. A dye composition according to claim 21 wherein the composition is in the form of a liquid and further comprises water and an acid buffer, wherein the dye composition preferably has a pH from about 2 to about 8.

24. A dye composition according to claim 21 wherein the composition is in the form of a paste and further comprises water, thickening agent and an acid buffer, wherein the dye composition preferably has a pH from about 2 to about 8.

25. A dye composition according to claim 23 wherein the pH is preferably from about 2 to about 3.

* * * * *